(12) United States Patent
Halaka

(10) Patent No.: US 9,693,694 B2
(45) Date of Patent: *Jul. 4, 2017

(54) CANCER CELL DETECTION USING DIELECTROPHORETIC DYNAMIC LIGHT SCATTERING (DDLS) SPECTROSCOPY

(71) Applicant: Folim G. Halaka, Burr Ridge, IL (US)

(72) Inventor: Folim G. Halaka, Burr Ridge, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/494,565

(22) Filed: Sep. 23, 2014

(65) Prior Publication Data

US 2015/0133794 A1  May 14, 2015

Related U.S. Application Data

(63) Continuation-in-part of application No. 13/683,924, filed on Nov. 21, 2012, now Pat. No. 8,843,186.

(51) Int. Cl.
| | |
|---|---|
| *A61B 5/1455* | (2006.01) |
| *A61B 5/00* | (2006.01) |
| *A61B 5/05* | (2006.01) |
| *A61B 5/145* | (2006.01) |
| *B03C 5/00* | (2006.01) |
| *B03C 5/02* | (2006.01) |
| *G01N 15/02* | (2006.01) |
| *G01N 15/00* | (2006.01) |

(52) U.S. Cl.
CPC .......... *A61B 5/0093* (2013.01); *A61B 5/0507* (2013.01); *A61B 5/1455* (2013.01); *A61B 5/14532* (2013.01); *A61B 5/7257* (2013.01); *B03C 5/005* (2013.01); *B03C 5/026* (2013.01); *A61B 2562/0233* (2013.01); *B03C 2201/26* (2013.01); *G01N 2015/0065* (2013.01); *G01N 2015/0222* (2013.01)

(58) Field of Classification Search
None
See application file for complete search history.

(56) References Cited

U.S. PATENT DOCUMENTS

| | | |
|---|---|---|
| 3,870,612 A | 3/1975 | Flygare et al. |
| 4,882,492 A | 11/1989 | Schlager |
| 4,901,728 A | 2/1990 | Hutchison |

(Continued)

OTHER PUBLICATIONS

International Preliminary Report on Patentability, PCT/US13/69354, Issued Jun. 4, 2015.

(Continued)

*Primary Examiner* — Eric Winakur
*Assistant Examiner* — Marjan Fardanesh
(74) *Attorney, Agent, or Firm* — Clifford H. Kraft

(57) ABSTRACT

Non-invasive apparatus and method for determining and monitoring glucose concentrations in human subjects. Glucose level is estimated through the effect of glucose on biological cells with glucose dependencies, e.g., red blood cells. The invention is based on the interaction of such cells with oscillating electric field gradients. The response of biological cells depends on factors including shape, size, and electrical charge distribution. The field gradient causes the cells to undergo characteristic motion which is detected by light beam scattering. The autocorrelation of the scattered light is computed, and the Fourier transform (FT) is performed to produce a characteristic velocity spectrum in which the peaks are characteristic of the cell "bio-electrical" states. The glucose level is estimated through measurements of changes of FT with changes in glucose levels after calibration with standard glucose methods.

3 Claims, 11 Drawing Sheets

(56) References Cited

U.S. PATENT DOCUMENTS

| | | |
|---|---|---|
| 5,009,230 A | 4/1991 | Hutchinson |
| 5,070,874 A | 12/1991 | Barnes et al. |
| 5,119,819 A | 6/1992 | Thomas et al. |
| 5,222,496 A | 6/1993 | Clarke et al. |
| 5,298,967 A | 3/1994 | Wells |
| 5,448,992 A | 9/1995 | Kupershmidt |
| 5,459,317 A | 10/1995 | Small et al. |
| 5,517,987 A | 5/1996 | Tsuchiya ............... 600/328 |
| 5,553,613 A | 9/1996 | Parker |
| 5,581,349 A | 12/1996 | Halaka |
| 5,703,364 A | 12/1997 | Rosenthal |
| 5,823,966 A | 10/1998 | Buchert |
| 6,016,435 A | 1/2000 | Maruo et al. |
| 6,043,492 A | 3/2000 | Lee et al. |
| 6,044,285 A | 3/2000 | Chaiken et al. |
| 6,061,582 A | 5/2000 | Small et al. |
| 6,181,957 B1 | 1/2001 | Lambert et al. |
| 6,377,828 B1 | 4/2002 | Chaiken et al. |
| 6,424,849 B1 | 7/2002 | Berman et al. |
| 6,424,850 B1 | 7/2002 | Lambert et al. |
| 6,445,938 B1 | 9/2002 | Berman et al. |
| 6,505,059 B1 | 1/2003 | Kollias et al. |
| 6,574,490 B2 | 6/2003 | Abbink et al. |
| 6,748,250 B1 | 6/2004 | Berman et al. |
| 6,841,389 B2 | 1/2005 | Novikov et al. |
| 7,050,847 B2 | 5/2006 | Ollmar et al. |
| 7,333,841 B2 | 2/2008 | Maruo et al. |
| 8,043,227 B2 | 10/2011 | Van Gogh et al. |
| 2002/0095075 A1 | 7/2002 | Madarasz et al. ............ 600/310 |
| 2005/0054907 A1 | 3/2005 | Page et al. |
| 2010/0130883 A1 | 5/2010 | Carpenter et al. |
| 2011/0208036 A1 | 8/2011 | Axelrod et al. |
| 2012/0116236 A1 | 5/2012 | Hogan |

OTHER PUBLICATIONS

PCT Search Report and Opinion (current case), PCT/US13/069354, Mar. 26, 2014, Supplied in Parent Case U.S. Appl. No. 13/683,924.

CANCER CELL DETECTION USING DIELECTROPHORETIC DYNAMIC LIGHT SCATTERING (DDLS) SPECTROSCOPY

This is a continuation in part of application Ser. No. 13/683,924 filed Nov. 21, 2012. Application Ser. No. 13/683,924 is hereby incorporated by reference in its entirety.

FIELD OF THE INVENTION

The present invention relates to measuring a medical parameter and more particularly to a cancer cell detection device.

DESCRIPTION OF THE PRIOR ART

Cancer diagnostics has long been a focus of academic and commercial research. The tools used to diagnose cancer cells are diverse, and span most of the known analytical and medical diagnostics instruments and techniques.

My U.S. Pat. No. 5,581,349 describes a Method for Biological Cell and Particulate Analysis. That patent was not concerned with cancer cells per se; however, the techniques taught in that patent can be used with embodiments and devices of the present invention to detect and monitor cancer cells both in-vitro, in-vivo, and non-invasively.

Commonly, many imaging techniques are used in all phases of cancer management, as reviewed by L. Fassa, *Molecular oncology*, 2 (2008) 115-152

Because of the importance of the subject of cancer detection, many patents are published. The majority of patents use electromagnetic radiation, ultrasound, and magnetic resonance imaging (MRI). Numerous literature address targeting cancer cells with an attachable molecule that is able to emit a signal, e.g., fluorescence.

For example, U.S. Pat. No. 8,663,929 describes Method for detection of liver cancer cell using anti-glypican-3 antibody, where in the binding may be indicated by methods selected from nuclear magnetic resonance (NMR) spectrometry, gas chromatography-mass spectrometry (GC-MS), liquid chromatography-mass spectrometry (LC-MS), correlation spectroscopy (COSy), nuclear Overhauser effect spectroscopy (NOESY), rotating frame nuclear Overhauser effect spectroscopy (ROESY), LC-TOF-MS, LC-MS/MS, and capillary electrophoresis-mass spectrometry. In certain preferred embodiments, the panel of metabolic biomarkers includes biomarkers that have been identified by nuclear magnetic resonance (NMR) spectrometry and liquid chromatography-mass spectrometry (LC-MS).

U.S. Pat. No. 8,653,006 describes metabolite biomarkers for the detection of esophageal cancer using NMR Methods for the detection and screening of esophageal adenocarcinoma (EAC) patients and for the monitoring of EAC treatment using a panel or panels of small molecule metabolite biomarkers are disclosed. In other aspects, methods for detection and screening for the progression of high-risk conditions (BE and HGD) to EAC and to monitoring treatment using a panel or panels of small molecule metabolite biomarkers are disclosed. The biomarkers are sensitive and specific for the detection of EAC, and can also be used to classify Barrett's esophagus (BE) and high-grade dysplasia (HGD), which are widely regarded as precursors of EAC.

U.S. Pat. No. 8,642,009 describes diagnostic system for the detection of skin cancer, where a composition comprising a florescent probe that binds to a specific neoplasia associated marker is applied topically to the area of interest. After topical administration, the probe preferentially binds to markers associated in neoplastic lesions in situ, which binding is detected with a compact illumination unit that provides illumination at a wavelength appropriate for image acquisition. The illumination unit comprises a light source and fiber optic bundle to direct the light towards the area of examination. A detection unit is used to capture and record an image of the area of investigation. The detection unit may be a digital camera, film camera, etc. A mapping module may also be provided to catalogue the site of examination.

U.S. Pat. No. 8,447,379 describes imaging of cells such as cancer and other biologic substances using targeted nanoparticles and magnetic properties, comprising exposing a sample to a plurality of targeted nanoparticles, where each targeted nanoparticle comprises a paramagnetic nanoparticle conjugated with one or more targeting agents that preferentially bind with the biological substance, under conditions that facilitate binding of the targeting agent to at least one of the one or more biological substances. This is followed by subjecting the sample to a magnetic field of sufficient strength to induce magnetization of the nanoparticles and measuring a magnetic field of the sample after decreasing the magnetic field applied in step b below a threshold. Superconducting quantum interference device (SQUID) magnetic sensors are used.

SUMMARY OF THE INVENTION

In the present invention, a detection scheme to distinguish cancerous cells from normal cells is presented through the application of Dielectrophoretic Dynamic Light Scattering (DDLS) Spectroscopy. When a biological cell is placed in an oscillating electric field gradient, the cell undergoes characteristic motion as electrical dipoles rearrange to follow the electric field oscillations. The motion of the cell, referred to as dielectrophoresis, is characteristic mainly of the cell's size and electrical charge distribution inside and on the cell surface. The motion also depends on the frequency of field oscillation, field strength, and spatial field gradient. By field gradient it is meant an electric field gradient, although other fields may be used such as a magnetic field. In this invention, the motion is detected by light scattering, typically laser light. The autocorrelation of the scattered light is computed; and, a Fourier transform (FT) is constructed to produce a characteristic velocity spectrum, in which the peaks in the FT are characteristic of cell "bio-electrical" states. Additionally procedures for correlating the FT peaks to cell conditions, particularly as related to "normal cells" are described. A brief description of the main components mentioned above is presented herein. The analytical method of using autocorrelation of scattered light from a solution containing particles with an applied non-uniform electric field is described in my U.S. Pat. No. 5,581,349 and is applied herein to a device that can identify and monitor cell states.

BACKGROUND OF THE INVENTION

Behavior of Biological Cells in Oscillating Electric Field Gradients:

As described in my U.S. Pat. No. 5,581,349, particles placed in a uniform electric field behave in a predictable manner—the familiar electrophoresis. If the particles carry a net charge, they move toward an electrode of opposite polarity; they do not move if they carry no net charge, even if the particles are polarizable. Polarizability is the ability of charges on or inside particles to move in response to the application of external electric fields, to form electric dipole(s). If the electric field is uniform, equal and opposite forces are exerted on each end of the resulting dipole, i.e., polarizability does not influence electrophoresis.

If the electric field possesses a spatial gradient, unequal forces will be experienced by each end of the dipole, leading the particle to undergo net translational motion in the direction of the maximum in the field gradient (dielectrophoresis), even if the polarizable particle is, overall, electrically neutral. Furthermore, when the applied field gradient is oscillating at certain frequencies (typically in the radio frequency (RF) range, the particle continues the translational motion in the same direction, as illustrated in FIGS. 1A and 1B, where a field gradient is formed by the choice of shape/geometry of electrodes (11 and 12). The field gradient is imposed on polarizable cells (13 and 15), forcing motion of the cells toward the anode 12 (FIG. 1A). When the polarity of the electric field is reversed (FIG. 1B), where now electrode 12 is cathode, the polarizable cells (13 and 15) experience a similar effect, but keep moving toward maximum field gradient, i.e., the cells do not reverse direction with reversal of field polarity.

Dielectrophoresis depends on biological cell conditions, particularly changes in the dielectric properties of cells, and has been the subject of numerous studies, see [5], for review. In the treatment of the effect of oscillating electric fields on biological systems, a great number of studies have focused on the detection, by electrical means, of the changes in the electrical properties of the biomolecules.

Many neutral and charged particles (e.g., biological cells) are polarizable; polarization can occur through movement of electrically charged constituents: inside the cell, on the cell surface, or by influencing the electrical double layer surrounding the cell[1,2]. For these reasons, and because they contain numerous charged molecules, most biological cells are polarizable. Furthermore, the motion is frequency-dependent, and is maximized at certain frequencies. These properties present unique and advantageous applications in the present invention, as the motion of a particular population of cells can be selected to "resonate" at certain frequencies. The motion is maximized when the frequency matches the (inverse of) the time it takes for charges to rearrange (relaxation time).

As described in my U.S. Pat. No. 5,581,349, the force exerted by the electric field on the cell depends on several factors including intrinsic properties of the cell such as size, shape, and polarizability. The force also depends on external (experimental) factors such as the field strength, gradient, and the properties of the suspending medium. The force F can be represented as:

$$F = 2\pi r^3 g \in_m \nabla E^2 \quad (1)$$

Where r is the particle's radius, $\in_m$ is medium's dielectric constant, and E is the electric field strength. Equation 1 indicates that the force is proportional to the volume of the cell. It can be seen that the force depends on both the field strength and on the field gradient, as $\nabla E^2$ may also be written as $2E\nabla E$. g is a function of the electrical permittivities of the particle and the medium:

$$g = g(\varepsilon_m^*, \varepsilon_p^*) = \text{Re}\frac{(\varepsilon_p^* - \varepsilon_m^*)}{(\varepsilon_p^* + 2\varepsilon_m^*)} \quad (2)$$

Where Re is the real part of the complex function, and $\in_p^*$ and $\in_m^*$ are the complex permittivities of the particle, p, and the medium, m, respectively. A force of sufficient magnitude that acts upon a particle causes particle movement, the speed of which indicates the magnitude of the force.

As can be seen from Equation 2, the direction of motion above is for the case where the absolute values of $\in_p^* > \in_m^*$, (where the particles are more polarizable than the medium). In instances, such as here, where the particle is more polarizable than the medium, the particles migrate toward the minimum in the field gradient.

Dynamic Light Scattering:

To study the force in a quantitative manner (as manifested by the resulting velocity of the particle movement), dynamic light scattering (DLS) can be employed. In DLS, a light beam, typically from a laser, impinges on a solution of particles, and the intensity of the scattered light is measured at a specified angle. The frequency of the scattered light is Doppler shifted due to the Brownian motion of the scattering particle. The frequency shifts are related to the diffusion coefficients of the particles in the medium. DLS experiments measure the Fourier transform (FT) of these frequency shifts[3] as the time-domain autocorrelation function, $C(\tau)$.

$$C(\tau) = \langle N^2 \rangle e^{-q^2 D \tau} \quad (3)$$

Where <N> is the average number of particles per unit volume, θ is the angle between the incident and the scattered beam (defined by detector position), D is the diffusion coefficient, τ is the delay time, and q is an experimental constant related to the light arrangement and the medium:

$$q = \frac{4\pi n}{\lambda} \sin\frac{\theta}{2} \quad (4)$$

Here, n is the refractive index of the medium, θ is the scattering angle, and λ is the wavelength of the light beam. The diffusion coefficient D for a spherical particle is:

$$D = \frac{kT}{6\pi\eta r} \quad (5)$$

where k is the Boltzmann constant, T is the absolute temperature, η is the viscosity of the medium and r is the particle's radius. Formula (5) is presented for reference even though particles such as red blood cells are not spherical. Similar relationships exist for non-spherical particles It is known that time autocorrelation functions of Brownian motion are smooth exponential functions and are characteristic of the diffusion coefficients of the scattering species, which are used as a measure of their size from the diffusion coefficient. Except for single (monodisperse) systems, $C(\tau)$ data will be a superposition of multiple exponentials. This drawback has historically restricted DLS from application to complex mixtures such as blood.

Dielectrophoretic Dynamic Light Scattering (DDLS):

The imposition of an oscillating electric field gradient on the particles introduces significant features into DLS. A directed (non-Brownian) motion introduces modulations into the exponentially decaying $C(\tau)$ measured in DLS experiments which adds new information. The resulting function $C'(\tau)$ is modulated since it incorporates sinusoidal (or other) OSCILLATIONS ONTO $C(\tau)$[4]:

$$C'(\tau) = C(\tau)\cos(q \cdot v\tau) \quad (6)$$

where v is the directed velocity exhibited by the particle under the application of the field gradient. Equation 6 analyses may be simplified by the FT after removal of the component of the spectrum due to the Brownian motion, $C(\tau)$. $C(\tau)$ is acts as a background dampening factor for the oscillation. Removing $C(\tau)$ produces new "v-space" spectrum. The new spectrum, henceforth DDLS, provides both qualitative and quantifiable means to measuring cell movement, and thus to cell's state, and can be used to predict changes in cell due to size, shape, membrane structure, and electrical charge distribution, and, particularly in the case of cancer cells, chromosomal disorder.

The present invention utilizes discernible spectral features of Equation 6 as a function of conditions of cancer cells as predicted from Equations 1, 3, and 6. The v-space spectrum can be utilized to indicate cell state.

Additionally, the peaks in the FT spectrum may be also assigned to particular species. Each polarizable population present would, in principal, contribute a peak in the spectrum. By choice of frequency, electrode configuration and other experimental embodiments, it is possible to achieve an experimentally distinguishable response from different constituents in a mixture as described in my U.S. Pat. No. 5,581,349.

The present invention presents significant advantages for the measurement and monitoring of cells, among them the detection scheme and the use of dynamically differentiated light scattering signal. This can be revealed from examining the parameters of equations 3 and 6. An important practical characteristic of these equations is that the "static" scattering, e.g., time-invariant scattering, can be removed using appropriate logic and data analysis tools without removing significant details from collected data.

The ability to target and identify the response of a particular population of cells is an important advantage of the present invention. This is accomplished through the response of cells to the particular frequency of the applied field gradient since many cell populations respond to particular frequency ranges. This enables the targeting of a particular cell population to be preferentially affected by the choice of the applied oscillating field gradient frequency. This contrasts prior art techniques which sums the response from all components in the sample and thus renders such prior art techniques susceptible to interfering biological material.

Another advantage of the present invention can be seen from the penetration of electric fields into dielectric material, e.g., skin, finger nails, and the like which enables non-invasive characterization of diseases caused by, or manifested in, changes in cell conditions. Additionally, no reagents may be consumed by application of the present invention.

BRIEF DESCRIPTION OF THE DRAWINGS

Attention is now directed to several illustrations that show features of the present invention.

Several drawings and illustrations have been presented to aid in understanding the present invention. The scope of the present invention is not limited to what is shown in the Figures.

DESCRIPTION OF THE PREFERRED EMBODIMENT

Figure 1:
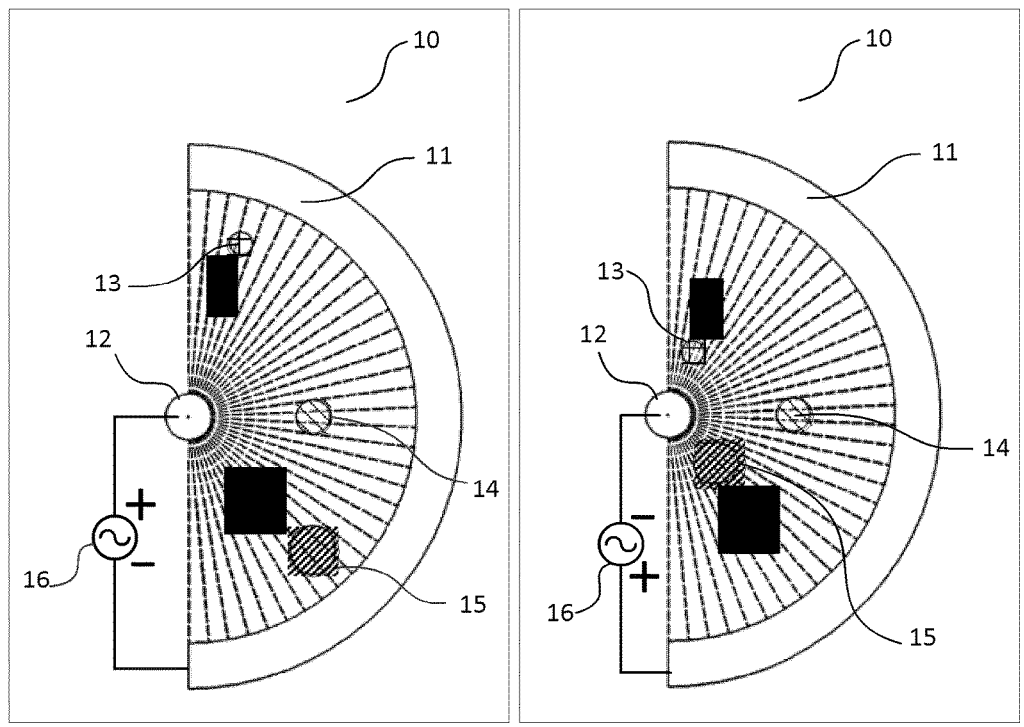
FIGS. 1A-1B show the effect of an electric field gradient on biological cells.

Turning to FIGS. 1A-1B, the effect of an oscillating electric field gradient on biological cells can be seen. The field gradient is formed by the choice of geometry and positioning of electrodes (11 and 12). The field gradient forces polarizable cells (13 and 15) toward the anode 12 (FIG. 1A). The direction of motion of cells is represented by corresponding arrows. When the polarity of the electrical field is reversed (FIG. 1B), polarizable cells (13 and 15) keep moving in the same direction (toward maximum field gradient) Unpolarizable cell 14 is unaffected. The electric field lines are presented as the dashed lines in FIGS. 1A and 1B.

An embodiment of the present invention contains a device with electrodes similar to the electrodes in FIGS. 1A and 1B, where the electrodes are connected to an oscillating power supply for creating an oscillating electrical field gradient with frequency preferably between 0 Hz and 100 GHz, more preferably in the radio frequency (RF) range between 3000 Hz to 3 GHz, and finally more preferably between 10 KHz and 100 MHz. The frequency of the oscillating power supply may be adjusted to maximize the movement of a particular cell population. The oscillating power supply (16) is selected to be capable of providing an electrical potential with amplitude at least from approximately 1 volt p-p up to at least 1000 volts p-p. The oscillating power supply, in combination with the electrode arrangement, provides a field gradient between 100 V/cm$^2$ and 10$^9$ V/cm$^2$, and preferably between 10$^3$ V/cm$^2$ and 10$^5$ V/cm$^2$. The high magnitudes of the field gradients are possible because the gap between the electrodes is small. In an embodiment of the present invention, the electrodes are comprised of noble metal, e.g., platinum (Pt) and may be shielded by a suitable insulator. The edge of one of the electrodes may be displaced from the edge of the other electrode so as to create a non-uniform field. Preferably, the electrodes are arranged as a ring or partial ring in a manner similar to that depicted in FIGS. 1A-1B or FIG. 6. In a preferred embodiment, the electrodes are aligned so that a part of the incident light beam (23 in FIG. 2, 60 in FIG. 7) reflects from the tip of an electrode (or elsewhere) to create a heterodyne mode known in the art[3].

In various embodiments, the electrodes may be shielded, preferably for non-invasive measurements on the (human) body and for application to non-invasive cancer detection by applying field gradient across specific areas of human body.

Figure 2:
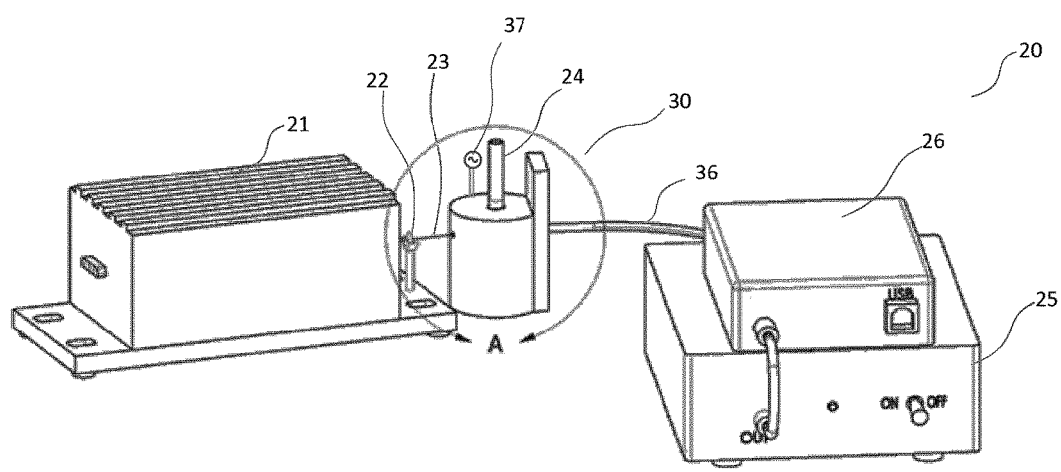
FIG. 2 shows components of a "desktop" DDLS instrument setup according to the present invention.
Figure 3:
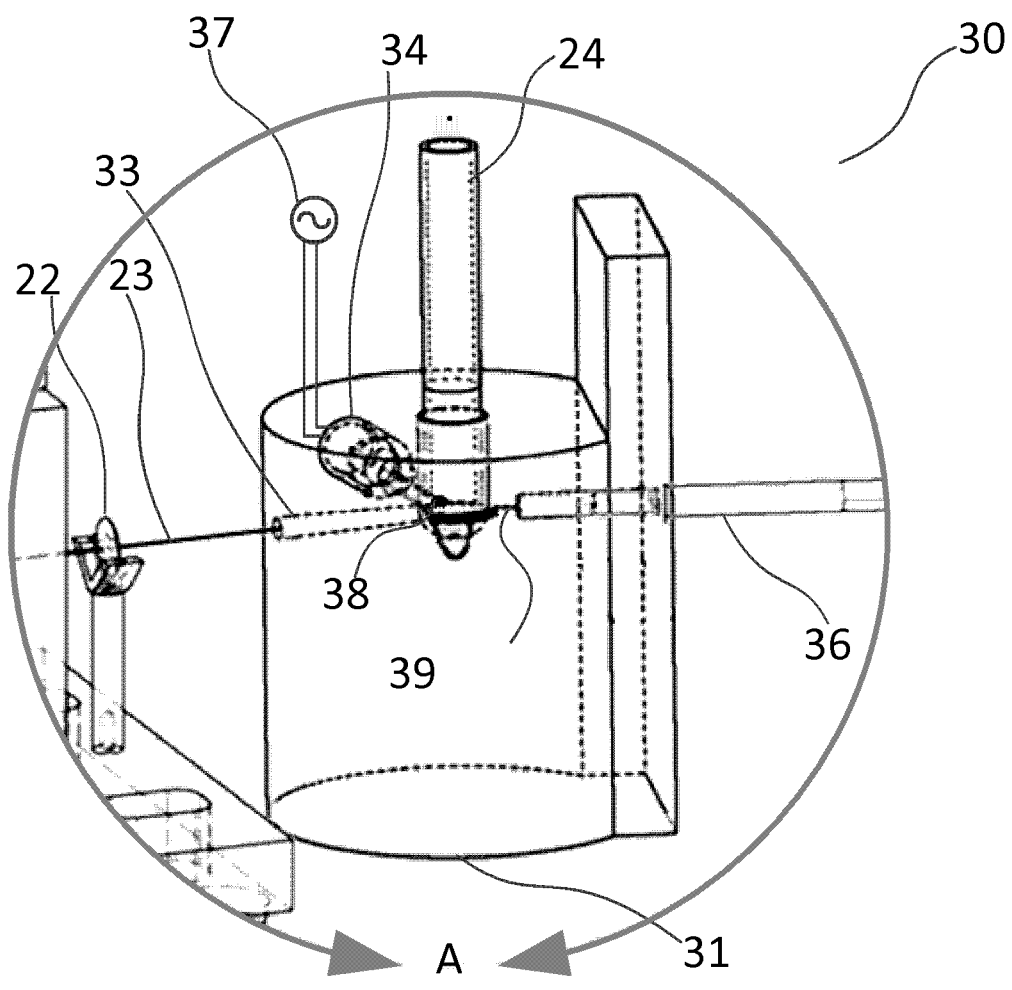
FIG. 3 is an enlarged view of the scattering vessel assembly depicted in FIG. 2.
Figure 4:
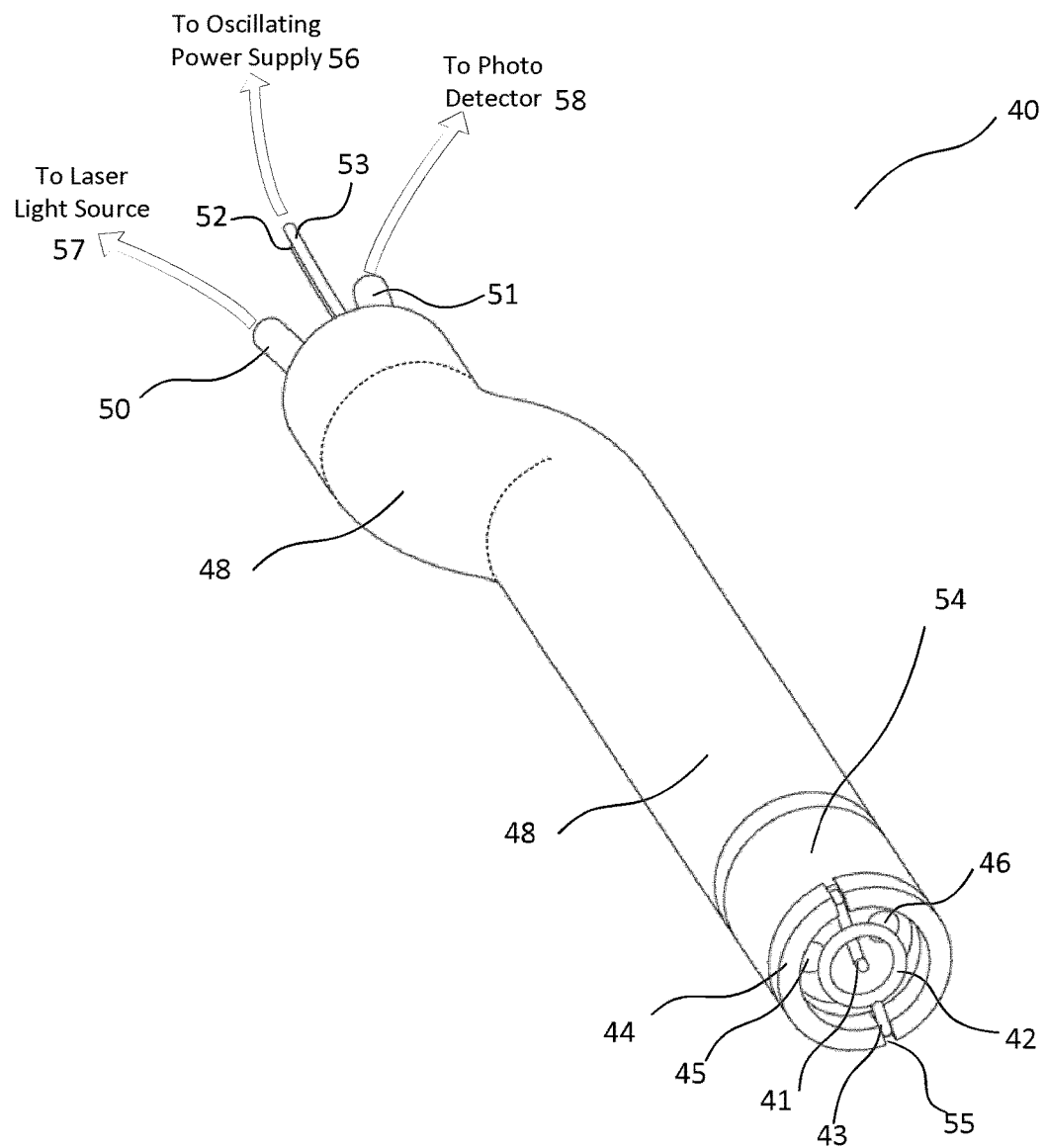
FIG. 4 is shows the components of a non-invasive device according to the present invention.

FIG. 2 shows a desktop DDLS instrument 20 to characterize biological cells according to the present invention. The instrument components include a laser 21 to produce a collimated incident beam of light 23, which may be focused through lenses 22. The incident laser beam may alternatively be conveyed using an optic fiber. Laser beam 23 enters sample vessel assembly 30 which is further detailed in FIG. 3. In FIG. 3, a laser beam 23 enters an opening 33 in support 31 where the beam impinges on sample vessel 24 containing biological material of interest. Part of the beam 23 scatters off electrode 38 to generate a heterodyne mode that allows easy detection and correlation. An electric field gradient is created between electrodes 38 and 39 by oscillating power supply 37 which is connected to the electrodes through connector 34. Scattered light 27 is collected in optical fiber 36.

Returning to FIG. 2, optical fiber 36 connects to a photodetector 25, which may be a device that uses the photoelectric effect to convert radiant energy into an electrical signal such as a photodiode or a phototube. Photodetector 25 is preferably a photon counting photomultiplier tube (PMT) or preferably an avalanche photodiode (APD). Any light detecting method or device is within the scope of the present invention. The electrical signal from the photodetector enters digital correlator 26 which constructs the autocorrelation function (Equations 3 and 6). The output of the digital correlator is digitized usually by an analog to digital converter (A/D converter) and analyzed by logic, typically in a processor, to correlate the autocorrelation functions to cell spectrum data from stored calibration curve or to take a Fourier Transform (FT) and correlate spectral peaks. A microprocessor, microcontroller, digital signal processor or other processor with appropriate programming is generally used for such tasks. Preferably the analysis uses the Fourier Transform FT as discussed above. Fourier Transforms can conveniently be realized by algorithms known as Fast-Fourier Transforms (FFT). Various windowing and zero-padding techniques known in the art may be used to aid in taking the FT.

The system shown in FIG. 2 can be used to characterize the parameters of oscillator frequency, field strength (and oscillator voltage), gradient strength, beam wavelength, laser power and other necessary parameters such as refractive index and viscosity of the subject material.

Characterization of the above parameters enables the utilization of these parameters in the non-invasive operation of the present invention. For in-vitro measurements of cells in e.g., extracted blood sample, the sample is placed in the sample vessel 24 where the electrodes generate an electric field gradient after energizing the oscillating power supply 37. The sample vessel walls may be of glass, quartz, or clear plastic. The sample vessel may be immersed in a bath of refractive index-matching fluid, e.g., silicon oil. The temperature may be controlled by a thermoelectric (Peltier) device, such as those that can be obtained from TE Technologies of Traverse City, Mich., USA. An example of oscillating power supply 37 may consist of an electrical function generator producing an oscillating electrical signal (typically sinusoidal) which can be amplified by a broadband amplifier and fed to two electrodes 38 and 39. The field gradient is achieved by arrangement of the two mentioned electrodes in a fashion similar to that depicted in FIGS. 1A, 1B and FIG. 6. Those familiar with the art may construct field gradients in several other electrode configurations. The electrodes may be configured to produce a uniform gradient to minimize field gradient inhomogeneity in the scattering volume. In a preferred embodiment, the field gradient can range from $10^4$ $V^2/m^3$ to $10^{20}$ $V^2/m^3$ and preferably from $10^{12}$ to $5 \times 10^{15}$ $V^2/m^3$. Preferred oscillating electric field gradient strengths are chosen to cause polarization of the biological cells in specified areas of the body.

Figure 5:
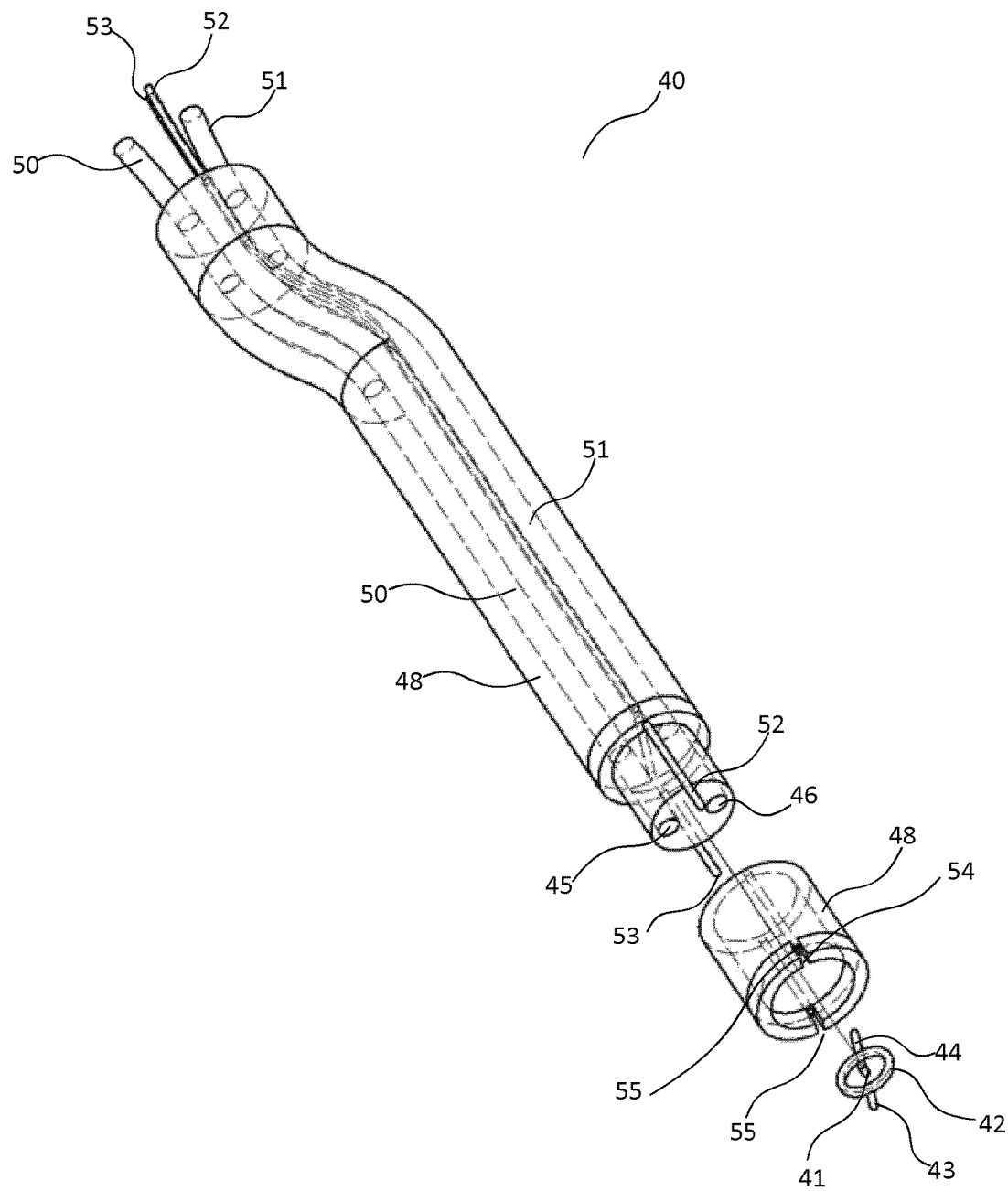
FIG. 5 is an exploded view of the non-invasive device depicted in 4 showing internal components.

FIGS. 4-7 show an embodiment for a device 40 for non-invasive measurement of cancer cells that are circulating in biological fluids, e.g., blood, in a non-invasive manner according to the present invention. FIG. 5 shows an exploded view of the device in FIG. 4 with the inner components outlined with dashed lines. Device 40 includes two electrodes 41 and 42 arranged to generate an electric field gradient. The oscillating electric power supply 56 (not shown in) is capable of generating an oscillating electrical field by supplying sufficient voltage to achieve sufficient field gradients. Electrode connectors 43 and 44 are seated in grooves 54 and 55 and connect to the oscillating electrical power supply 56 through connectors 52 and 53. The oscillating electrical power supply 56 (not shown) may include an electrical function generator which generates a sinusoidal electrical wave, a square or triangular wave, or any other waveform, which is fed to an electrical signal amplifier to adjust the electrical waves' amplitude. For safety, the voltage between the tip and ground should not exceed recommended safe medical levels. If the tip is properly insulated, at least 40 V p-p may be used. The maximum allowed voltage will vary from country to country based on national safety standards. The connection is achieved by assembling the electrodes into guiding grooves 54 and 55. When the oscillating electric power supply 56 is energized, the oscillating electrical voltage supplied to the two electrodes 41 and 42 causes the creation of an oscillating electric field gradient.

Figure 6:
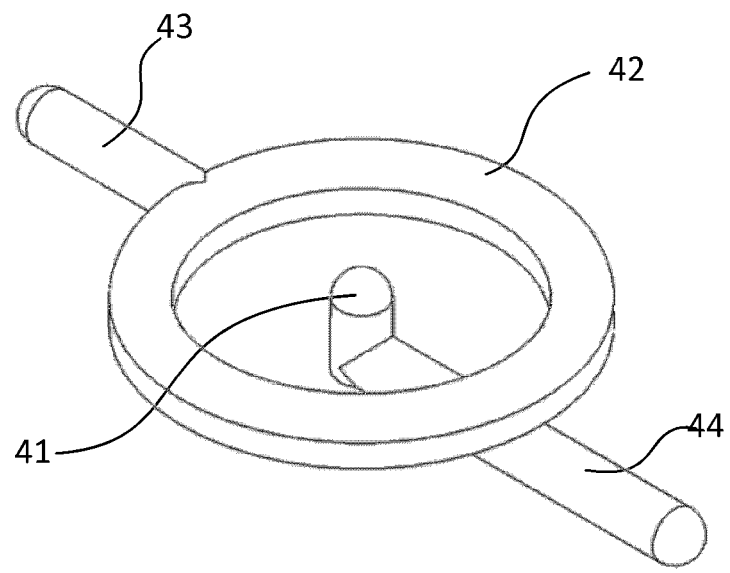
FIG. 6 is an exploded view of the electrode assembly shown in FIG. 5.

The electrodes are further illustrated in FIG. 6, where electrodes 41 and 42, due to their geometrical ring or partial ring shape, create a field gradient when connected to the electric power supply. Other electrode configurations, such as the configuration in FIGS. 1A-1B, may also be used. The electrodes and fiber optics configuration at the end that interacts with specific areas of body may be optionally thermostated to allow performing measurements at specified temperatures.

Figure 7:
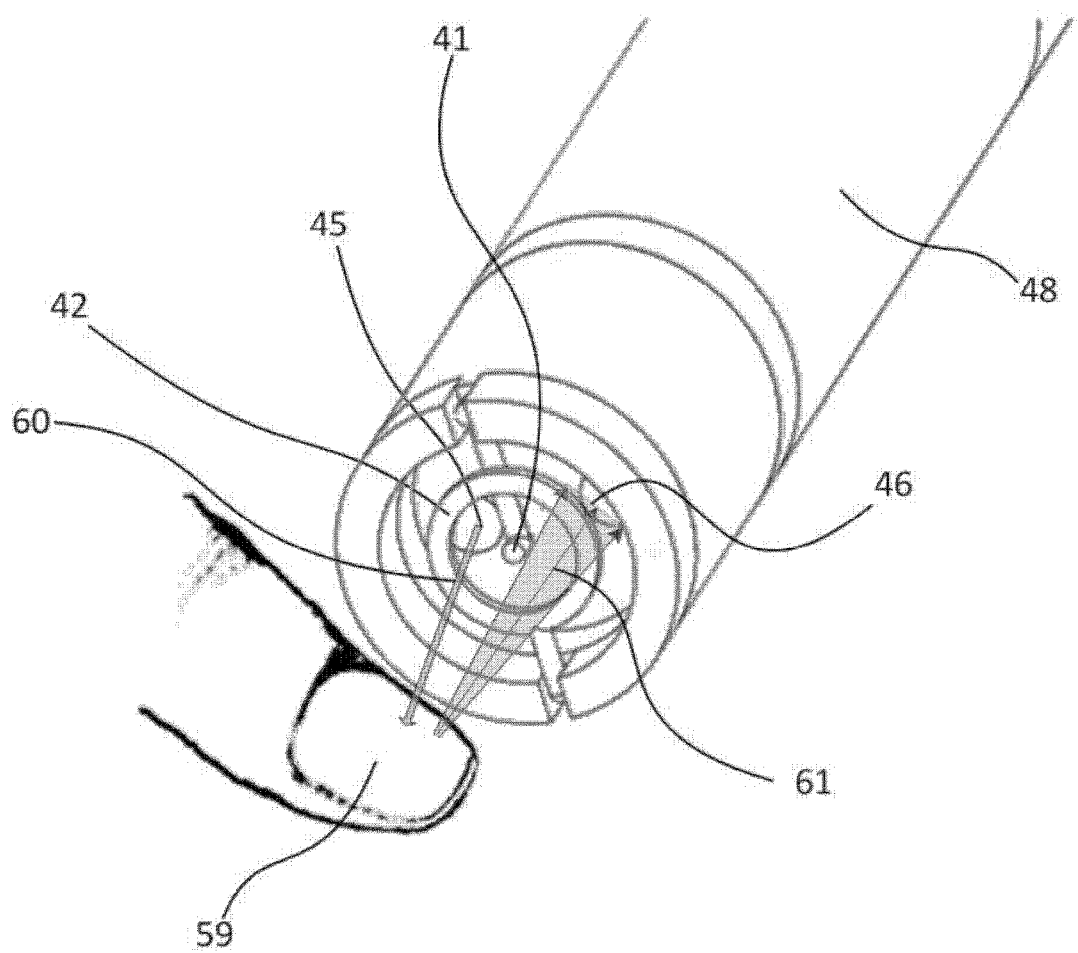
FIG. 7 is a detailed view of the application of the device in FIG. 6 to non-invasive measurements on the thumb nail area.

Referring to FIG. 7, electrodes 41 and 42 can be placed in a specified position, e.g., distance and orientation, with respect to a specified area of the body, such as finger nail, forearm, cheek, palm, stomach skin, earlobe, eye's humor etc. It is preferred that the two electrodes be safely insulated, and that the distance from the specific body part be as small as possible, preferably between 0 and 5 mm. A clamp may be used to repeatably position the electrodes in the specified position with respect to the specified area of the body.

Figure 11:
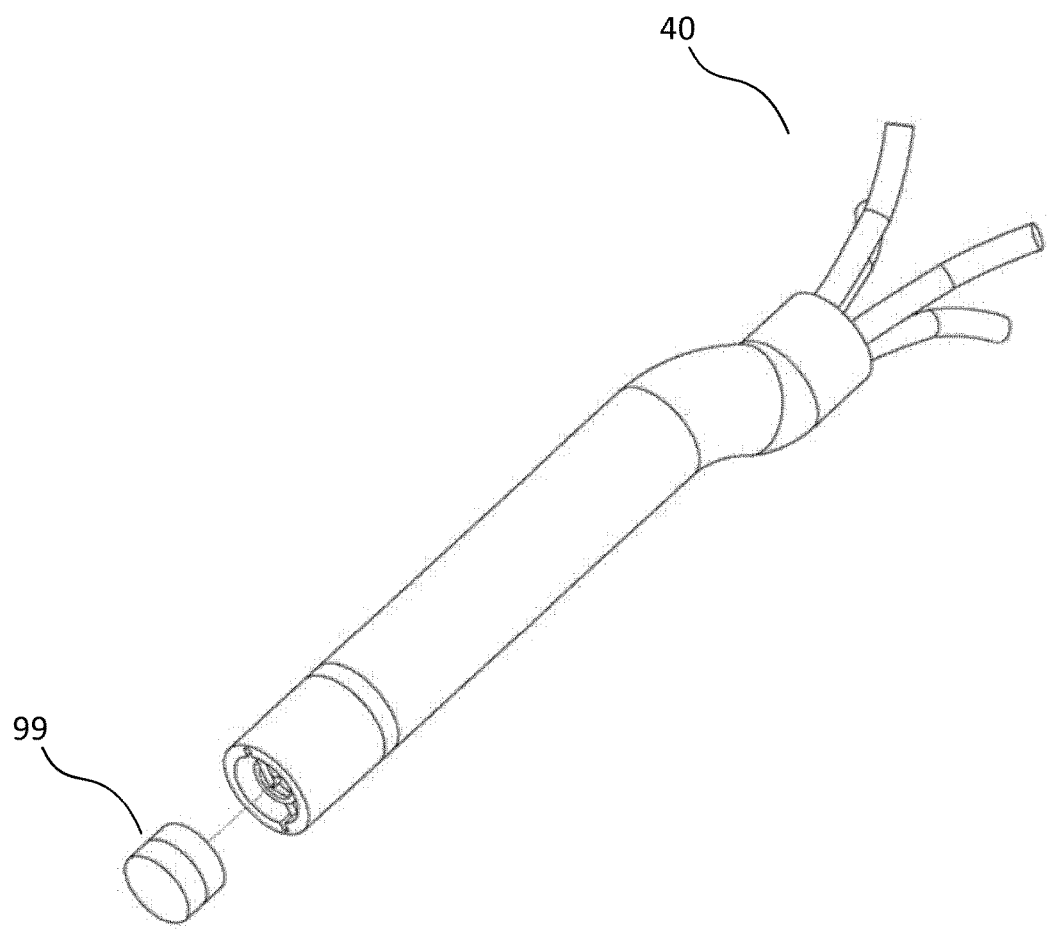
FIG. 11 is a view similar to that in FIG. 7, detailing application to cancer detection in-vitro.

In FIG. 11 show an embodiment for a device 40, similar to that in FIG. 7, and wherein it is used for in-vitro cancer cell detection for a sample containing cancer cells and place in specimen cell 99.

Returning to FIG. 4, the light source 57 (not shown) is preferably a laser, and preferably a solid state, single mode laser (such as may be provided by e.g., Quartron, Inc., Chino, Calif., USA). While a laser is the preferred light source, any light source is within the scope of the present invention. Light source 57 may produce collimated light with a wavelength in the near UV, visible, or near infrared regions. Different wavelengths can be used with different tissue or sample types. The incoming light can be coupled through an optical fiber cable 50, where the light beam is transmitted to impinge on the sample of interest. Incident light is scattered by the sample, and the scattered light can be transmitted through optical fiber cable 51 to a photodetector 58, such as a PMT or an APD (such as that provided by e.g., Hamamatsu Photonics K.K., Hamamatsu City, Japan). Additionally, flat surface Gradient-index (GRIN) lenses 45 and 46 may also be used for efficient coupling of the incident light and the scattered light to the optical fiber cables 50 and 51, respectively. Optical fiber cables and electrode wires are preferably enclosed in a flexible conduit for ease of orienting and positioning of the device with human body parts. At one end, a flexible part of conduit 49 encases the wires connecting electrodes 41 and 42 to the oscillating electrical power supply 56, and the optical fiber cables 50 and 51 to light source 57 and photodetector 58 respectively. At the other end of the conduit, a rigid portion 48 encases the electrode and fiber optics in a fixed configuration to ensure repeatability and ease of positioning with respect to the specified body part. Lens or optical fiber end 45 focuses the beam on the target. Lens or optical fiber end 46 collects the scattered light.

Scattered light from the interaction of the incident light beam with specific areas of the body is affected by the motion of biological cells, e.g., in blood, ISF, or serum. Since the cells are also affected by the electric field gradient, the scattered light contains information pertaining to the scattering cells. Therefore, analysis of the scattered light produces correlation to the status of cell state. The scattered light, collected at a specified angle $\theta$, is converted by a photodetector 58, to electric signals. The electric signals may be digitized by an analog-to-digital converter as known in the art, and may be integrated with the photodetector and a correlator to a construct time autocorrelation functions. The photodetector 58 is preferably a photon-counting PMT or an APD.

The autocorrelator output may be used by a computer or other processor with logic to further analyze the autocorrelation functions by the construction of a FT and storing the resulting velocity spectra for comparison with calibration data or as databases.

FIG. 7 shows an enlarged schematic of the bottom end of an embodiment of the present invention which details the application of the device to non-invasive measurement by positioning the device on or above the thumb nail area 59. Electrodes 41 and 42 are positioned at close distance from a translucent area of the body, e.g., thumb nail 59. With the oscillating power supply energized, an oscillating electric field gradient is created in the tissue under the thumbnail. Incident light beam 60 impinges on and is scattered by cells that respond to the applied field gradient. The scattered beam 61 enters fiber optic through 46 and travels to the photodetector. To ensure repeatability, the position of the device with respect to the body part, e.g., the thumb nail, may be aided by marking and clamping accessories. A computer or other processor with appropriate logic and software algorithms may be utilized to perform the data analysis previously discussed.

In the case of circulating cancer cells, the present invention provides a method for their non-invasive indication by the response of biological cells to the application of an oscillating electric field gradient on a specified area of the human body. Preferred areas of the body are characterized by being slightly opaque or translucent to allow for moderate penetration of the light beam into the tissues and the escape of the scattered light from areas of the body with biological cells-containing fluids such as blood, serum, and ISF. Examples of suitable areas of body include, but are not limited to, the finger nails, forearm, cheek, palm, stomach skin, earlobe, or the eye. It is preferable that the same areas be repeatedly used.

A preferred method for data analysis and display of DDLS measurements includes constructing a normalized function, $C'_{norm}(\tau) = [(C'(\tau)_\tau - C'(\tau)_{\tau=\infty}]/[C'(\tau)_{\tau=0} - C'(\tau)_{\tau=\infty}]$, where $C'(\tau)_{\tau=0}$ is the value in the first channel of the correlator, and $C'(\tau)_{\tau=\infty}$ is the value in the delay channel. The spectrum due to the Brownian motion may be estimated by curve-fitting $C\zeta_{norm}(\tau)$ to an exponential function which is the functional form of $C(\tau)$ The curve fitting may be accomplished by, for example, non-least square minimization procedure using special software or commercial software such as Microsoft's EXCEL Solver add-in (Microsoft, Redmond, Calif., USA). The oscillations due to DDLS (the term $e^{-iq \cdot v \tau}$ in Equation 7) can be obtained by dividing $C'_{norm}(\tau)$ by the exponential estimation of $C(\tau)$. This can be important in removing the static scattering components in addition to reducing the occurrence of low frequency peaks in the FT. The FT analysis can then be applied to the resulting function, and preferably, the FT is performed on the functional form: $[(C_{norm}'(\tau)/C_{norm}(\tau))-1]$ to render the oscillations symmetrical around zero and to minimize high frequency ripples (or side lobes) due to the presence of sharp truncation functions. In some cases, "zero filling or padding", or window functions may be used to improve the resolution in the FT and remove artifacts such as those caused by Gibbs phenomena known in the art. The velocities in the FT spectrum may be normalized (using the applied field strength and gradient) to correlate measurements under different conditions. The FT thus, under specified conditions, presents a "finger print" of the sample. Peaks in the FT may be assigned to particular components, e.g., specific cancer cell. The peaks can then be used to study changes to the specified components due to cancer effects. The data analysis scheme just described is preferred, although other analyses and algorithms familiar to those skilled in the art may be applied.

An important component of the present invention is to the construct a "calibration" to correlate the measurements made with the instrument of the invention with established cancer cell measurements using other validated technologies, e.g., imaging, CT scan, MRI, etc. In one embodiment, the calibration measurements are used to construct a look-up table, or "calibration look-up table", from correlation of peaks in the FT spectra to specific cancer cell state. Alternatively, a mathematical equation that can be called a "calibration equation" can be constructed from fitting observed data.

In an embodiment of the current invention, a method of correlating non-invasive DDLS measurements to validated technologies is presented, thus establishing a reference procedure, and may be used according to the following steps:
  i—measure "normal cells" using current validated method at standard physiological conditions;
  ii—use the device described in FIGS. 4-7 to:
    a. determine the time-dependent autocorrelation function $C(\tau)$ without the application of the electric field on the specific area of body per the data analysis scheme mentioned above;
    b. generate an oscillating electric field gradient of a specified frequency, electric field strength and field gradient and apply to the specific area of body;

c. measure the time-dependent autocorrelation function C'(τ) under the influence of the applied field gradient per the data analysis scheme mentioned above;

iii—construct a correlation table of DDLS measurement data vs. validated cancer measurements.

The present inventions may be also applied to other areas such as the identification of biological cells, biological macromolecules and polymeric substances.

For example, the present invention affords a method by which biological cells are identified by their FT spectrum under normalized conditions of electric field strength, electric field gradient, applied light source, frequency, and the like. The response of the biological cells to the field gradient and the subsequent autocorrelation function measurement, data analysis procedures and FT spectral analysis can follow steps similar to those described in the above embodiments and using devices similar to those of FIGS. 2 and 7. Calibration methods include assignment of FT spectral features to normal biological cells, which may be used to identify such normal cells. Some biological cells are known to be "not-normal" by current medical conventions, and may also be characterized by applying procedures as outlined above. Conditions that would render a cell not-normal may include cancer, metabolic stress, aging, genetic diseases, and infection by bacteria, viruses or other infectants. Initially, the FT spectral response described is correlated with established or validated identification of biological cells with the methods presented in the present invention. The construction of a repository of correlated data allows the use of the present invention to detect cell conditions, and thus offers diagnosis of biological cell maladies including cancer, aging, genetic diseases, infectious diseases and other stresses.

Similar devices and methods may be applied by the present invention to the detection of infectious organisms such as bacteria and viruses.

The present invention may also be applied to the identification of macromolecules. By macromolecule it is meant a molecule of molecular weight above 50,000 Daltons, and preferably in the range of 100 kilo Daltons to 100 Giga Daltons. Of particular interest is the application to the detection of DNA molecules, particularly with the polymerase chain reactions (PCR). PCR produces elongated DNA macromolecules which are identifiable by the present invention, and using the embodiments depicted in FIGS. 2 and 7.

There are applications of the present invention to non-biological macromolecules and polymers, including industrial polymers and latex manufacturing, with methods and devices similar to those presented herein.

As mentioned above, the present invention presents a method to non-invasively detect circulating tumor cells, the detection of which currently presents a considerable challenge. The device in FIG. 7 can be applied, for example, after a signature of said cancer cells are identified (via FT). The electrodes are applied on translucent tissue where the passage of the cancer cells may be detected by their signature.

EXAMPLES

Example 1

Figure 8:
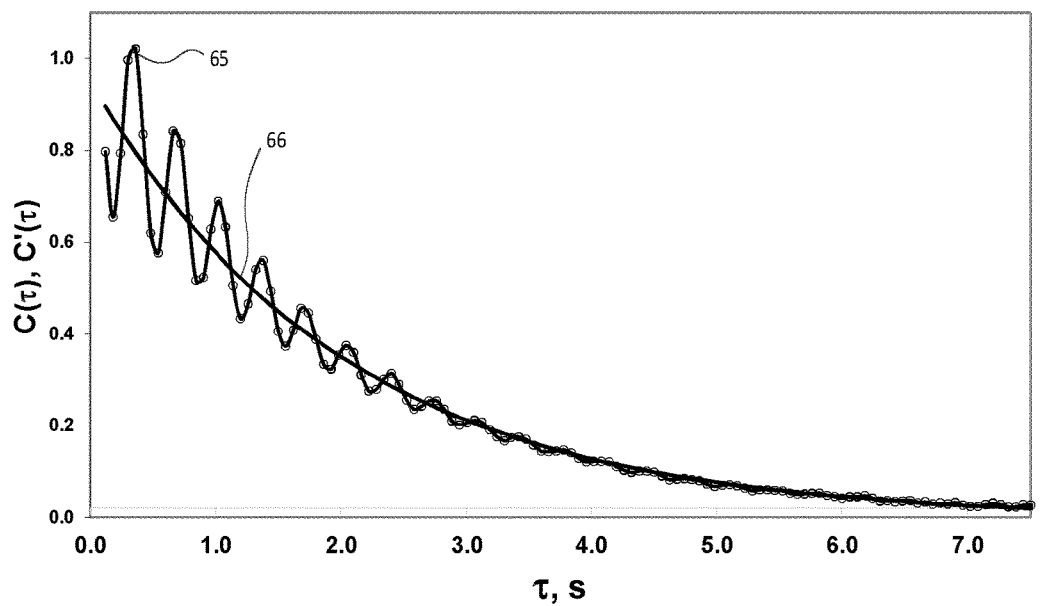
FIG. 8 is a graph showing an example of the effect of the application of an oscillating field gradient on the autocorrelation function of a suspension of $1 \times 10^{-6}$ gram/ml latex particles, of approximately 4.1 micron diameter in distilled water.

An example that illustrates the use of the device in 0 and associated data analyses is presented in FIG. 8, as applied to a suspension of $1\times10^{-6}$ gram/ml 4.1 microns latex particles. The particles were suspended in distilled water (conductivity ~30μ Semen/cm). Other parameters used: applied voltage: 40 V (nominal, peak-to-peak, as measured from the output of RF amplifier); frequency: 350 kHz; τ: 60 microseconds; and, θ=90°. For display, the normalized heterodyne autocorrelation functions were constructed from the correlator's raw data using the equation: $C'_{norm}(\tau)=[(C'(\tau)_{\tau}-C'(\tau)_{\tau=infinity}]/(C'(\tau)_{\tau=0}-C'(\tau)_{\tau=infinity})$, where $C'(\tau)_{\tau=0}$ is the value in the first channel of the correlator, and $C(\tau)_{\tau=infinity}$ is the value in the correlator's delay channel. In FIG. 8, is 66 is normalized C'(τ) and 65 is C(τ) per above description. C(τ) in this case was obtained from curve fitting of C'(τ) to an exponential function.

Example 2

Figure 9:
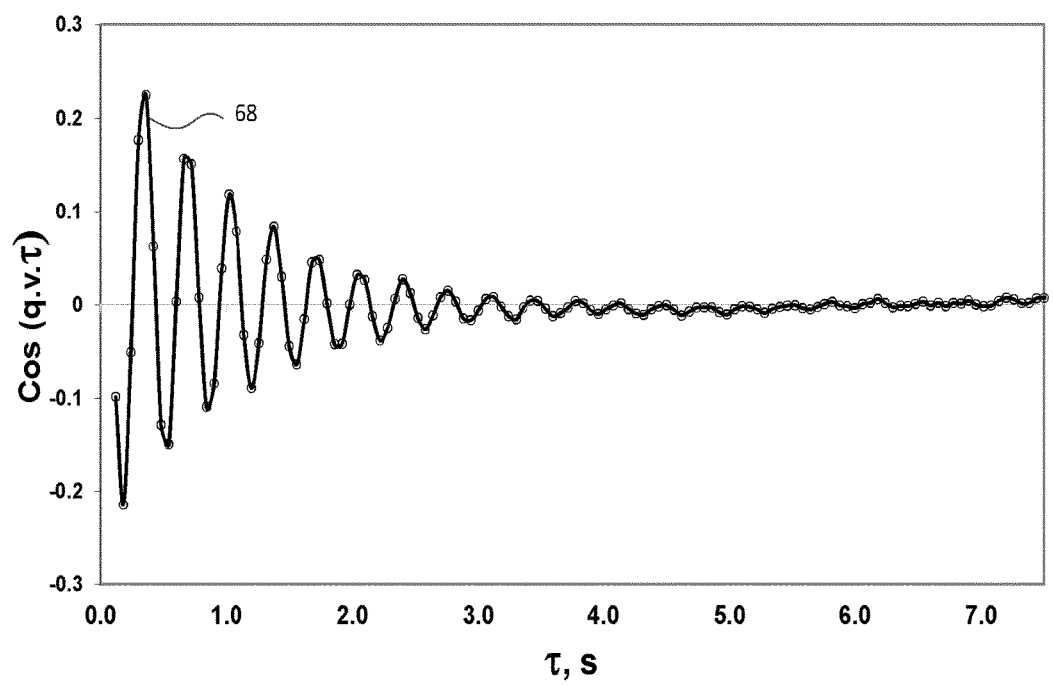
FIG. 9 is a graph of DDLS oscillations extracted from the data in FIG. 8 showing the oscillations due to the application of the field gradient.

The data in Example 1 were further analyzed by extracting the oscillations due to the application of the field gradient per the analysis schemes of this invention. FIG. 9 shows the extracted oscillations. The oscillations 68 in FIG. 9 were calculated as $[C'_{norm}(\tau)-1]$ to aid in the removal of spurious peaks in the FT. The FT showed a single peak, as expected. Improvements in the FT analysis may be accomplished by a weighting scheme, e.g., by dividing by the dampening factor C'(τ) as known in the art[6,7].

Example 3

Figure 10:
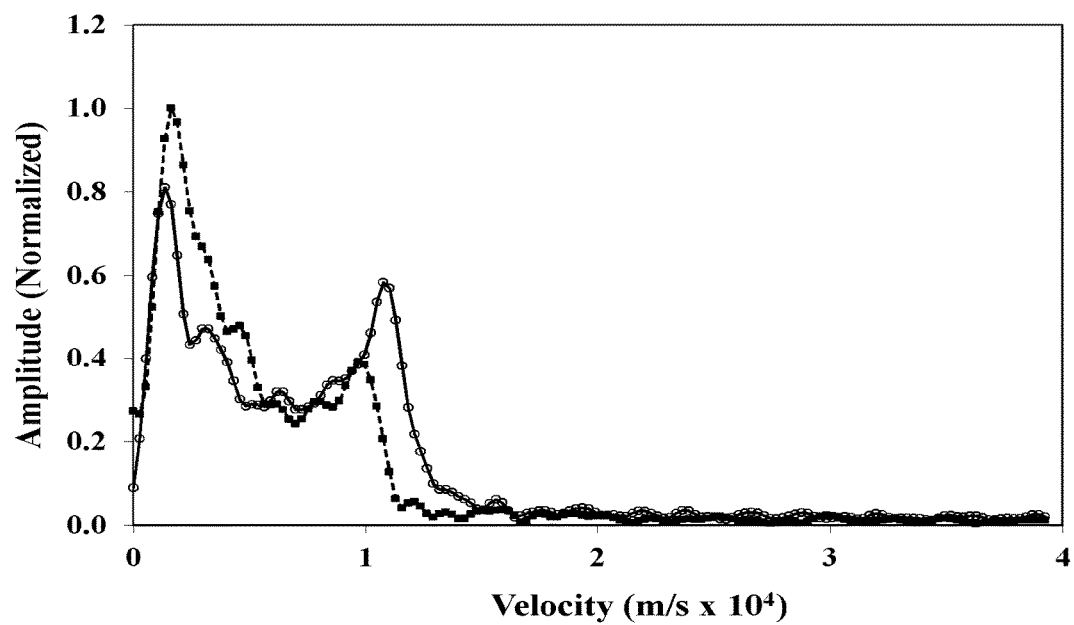
FIG. 10 is an example of the FT application to produce v-space spectrum as applied to a solution of yeast cells. 0.5 gram of Baker's yeast was suspended in 100 mL water and centrifuged at 2000 g for 10 minutes. The supernatant was discarded and the pellet resuspended (by vortexing) in 100 ml of water. The process was repeated once more and the suspension was. The measurements and data analysis were carried out as outlined herein.

FIG. 10 shows the application of the device presented in FIG. 2 and the data analysis procedures of the present invention as applied to a yeast cell mixture, with separate measurements using frequencies of 300 kHz and 500 kHz. A sample of Baker's yeast (0.5 gram in 100 ml water) was suspended in water and centrifuged at 2000 g for 10 minutes. The supernatant was discarded and the pellet resuspended (by vortex) in 100 ml of water. The process was repeated once and the suspension was used in the measurements, with other conditions similar to those in FIGS. 8-9. The isolated oscillations were extracted, and the FT (velocity domain) spectra of the oscillations are displayed. Trace 75 represents the spectrum from the application of oscillating field gradient of 300 kHz, while trace 76 is the spectrum resulting from the application of 500 kHz. Peak positions can be seen to depend on the frequency employed.

Several descriptions, illustrations and examples have been presented to aid in understanding the present invention. One with skill in the art will realize that numerous changes and variations may be made without departing from the spirit of the invention. Each of these changes and variations is within the scope of the present invention.

REFERENCES CITED

1. Pohl H. A., in "Dielectrophoresis," Cambridge University Press (1978).
2. Schwartz G., "A Theory of the Low Frequency Dielectric Dispersions of Colloidal Particles in Electrolytes Solution," *J. Phys. Chem.*, 66, 2636 (1962).
3. Berne B. J. and Pecora R., "Dynamic Light Scattering," Wiley-Interscience, New York (1976).
4. Halaka F. G., "Dielectrophoretic dynamic light-scattering (DDLS) spectroscopy," *Proc. Nat. Acad. Sci.* 100, 10146-10169 (2003).
5. Pethig, R., "Review Article—Dielectrophoresis: Status of the theory, technology, and applications", *Biomicrofluidics* 4, 022811 (2010).
6. Halaka, F. G., Boland, J. J. and Baldeschwieler, J. D., *J. Am. Chem. Soc.* 106, 5408-5413 (1984).

7. Boland, J. J., Halaka, F. G. and Baldeschwieler, J. D., *Phys. Rev. Lett.* 28, 2921-2926 (1983).

I claim:

1. A non-invasive apparatus for detection of cancer cells in a biological sample, said apparatus comprising:
   an elongated housing having a distal end and a proximal end;
   a pair of electrodes mounted at the distal end of the housing, the electrodes comprising an arcuate first electrode and a linear second electrode substantially centered in the arcuate first electrode;
   an oscillating power source constructed to produce a sinusoidal electric voltage; the oscillating power source electrically connected to said electrodes through a cable from the oscillating power source, through the proximal end of the housing to the electrodes;
   wherein said electrodes generate a non-uniform sinusoidal electric field between the arcuate and linear electrodes;
   a light source attached to the distal end of the housing constructed to deliver collimated light to a biological sample being exposed to said non-uniform electric field producing scattered light therefrom;
   a detector also attached to the distal end of the housing adapted to collect the scattered light;
   a processor mounted in said housing, the processor processing electrical signals from the detector related to the scattered light to produce an autocorrelation output signal, the processor comparing the autocorrelation output signal with stored autocorrelation signals taken from biological samples containing known cancer cells.

2. The non-invasive apparatus of claim 1 wherein said light source is a laser, and wherein said detector is a photomultiplier or a photo-diode.

3. The non-invasive apparatus of claim 1 wherein said oscillating electrical power source supplies an oscillating voltage of between approximately 1 volt and 1000 volts, and a frequency between approximately 0 Hz and 100 GHz.

* * * * *